US00PP14520P29

(12) United States Plant Patent
Drewlow

(10) Patent No.: US PP14,520 P2
(45) Date of Patent: Feb. 10, 2004

(54) NEW GUINEA IMPATIENS PLANT NAMED 'OVATION CHERRY ROSE'

(50) Latin Name: *Impatiens hawkeri*
Varietal Denomination: Ovation Cherry Rose

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 10/317,303

(22) Filed: Dec. 12, 2002

(51) Int. Cl.[7] ..... A01H 5/00
(52) U.S. Cl. ..... Plt./318
(58) Field of Search ..... Plt./318

*Primary Examiner*—Kent Bell
(74) *Attorney, Agent, or Firm*—C. A. Whealy

(57) ABSTRACT

A new and distinct cultivar of New Guinea Impatiens plant named 'Ovation Cherry Rose', characterized by its mounded plant habit; freely branching growth habit; dark green leaves; freely flowering habit with flowers positioned above or beyond the foliage; large, red purple-colored flowers; and tolerance to full sun conditions and low and high temperatures.

1 Drawing Sheet

Botanical classification/cultivar designation: *Impatiens hawkeri* cultivar Ovation Cherry Rose.

BACKGROUND OF THE INVENTION

The present Invention relates to a new and distinct cultivar of New Guinea Impatiens plant, botanically known as *Impatiens hawkeri*, and hereinafter referred to by the cultivar name 'Ovation Cherry Rose'.

The new Impatiens is a product of a planned breeding program Inventor in Ashtabula, Ohio and Lompoc, Calif. The objective of the breeding program is to develop new freely flowering Impatiens cultivars with interesting flower and foliage colors.

The new Impatiens originated from a cross-pollination made by the Inventor during the winter of 1997 of a proprietary *Impatiens hawkeri* seedling selection designated as code number 96-477-2, not patented, as the female, or seed parent, with a proprietary *Impatiens hawkeri* seedling selection designated as code number 97-299-5, not patented, as the male, or pollen parent. The cultivar Ovation Cherry Rose was discovered and selected by the Inventor as a flowering plant within the progeny of the stated cross in a controlled environment in Ashtabula, Ohio.

Asexual reproduction of the new cultivar by terminal cuttings taken at Lompoc, Calif., since August, 1998, has shown that the unique features of this new Impatiens are stable and reproduced true to type in successive generations. Plants of the new Impatiens differ from the parent selections in plant size and habit, leaf size and color, and flower size and color.

SUMMARY OF THE INVENTION

The following traits have been repeatedly observed and are determined to be the unique characteristics of 'Ovation Cherry Rose'. These characteristics in combination distinguish 'Ovation Cherry Rose' as a new and distinct Impatiens cultivar:

1. Mounded plant habit.
2. Freely branching growth habit, dense and full plants.
3. Dark green leaves.

4. Freely flowering habit with flowers positioned above or beyond the foliage.
5. Large, red purple-colored flowers.
6. Tolerant to full sun conditions and low and high temperatures.

Plants of the new Impatiens can be compared to plants of the cultivar Balcebchro, disclosed in U.S. Plant Pat. No. 11,919. In side-by-side comparisons conducted in Lompoc, Calif., plants of the new Impatiens differed from plants of the cultivar Balcebchro, in the following characteristics:

1. Plants of the new Impatiens were shorter than plants of the cultivar Balcebchro.
2. Plants of the new Impatiens had larger leaves than plants of the cultivar Balcebchro.
3. Plants of the new Impatiens had larger flowers than plants of the cultivar Balcebchro.
4. Plants of the new Impatiens had shorter flower spurs than plants of the cultivar Balcebchro.

Plants of the new Impatiens can also be compared to plants of the cultivar Noctua, disclosed in U.S. Plant Pat. No. 10,433. In side-by-side comparisons conducted in Lompoc, Calif., plants of the new Impatiens differed from plants of the cultivar Noctua, in the following characteristics:

1. Plants of the new Impatiens were shorter and more mounded (not as upright) than plants of the cultivar Noctua.
2. Plants of the new Impatiens had larger leaves than plants of the cultivar Noctua.
3. Plants of the new Impatiens had larger flowers than plants of the cultivar Noctua.
4. Flower color of plants of the new Impatiens was darker red purple than flower color of plants of the cultivar Noctua.
5. Plants of the new Impatiens had longer flower spurs than plants of the cultivar Noctua.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Ovation Cherry Rose' grown in a container.

DETAILED BOTANICAL DESCRIPTION

The cultivar Ovation Cherry Rose has not been observed under all possible environmental conditions. The phenotype may vary somewhat with variations in environment such as temperature and light intensity, without, however, any variance in genotype. The aforementioned photographs and following detailed botanical description describe plants grown in Lompoc, Calif., during the winter, under commercial practice in a fiberglass-covered greenhouse. Plants used in the following description were grown in 15-cm containers for about seven to nine weeks after planting rooted cuttings. During the production period, day temperatures were about 21 to 24° C., night temperatures were about 16 to 18° C., and light levels were about 3,000 to 4,000 foot-candles.

In the following description, color references are made to The Royal Horticultural Society Colour Chart, 1995 Edition, except where general terms of ordinary dictionary significance are used.

Botanical classification: *Impatiens hawkeri* cultivar Ovation Cherry Rose.

Commercial classification: New Guinea Impatiens cultivar Ovation Cherry Rose.

Parentage:

*Female parent.*—Proprietary *Impatiens hawkeri* seedling selection designated as code number 96-477-2, not patented.

*Male parent.*—Proprietary *Impatiens hawkeri* seedling selection designated as code number 97-299-5, not patented.

Propagation:

*Type cutting.*—Terminal cuttings.

*Time to initiate roots.*—Summer: About 10 days at 21° C. Winter: About 12 days at 21° C.

*Time to produce a rooted young plant, summer and winter.*—About 21 days at 21° C.

*Root description.*—Fibrous, white in color.

*Rooting habit.*—Freely branching, dense.

Plant description:

*General appearance.*—Mounded plant habit; numerous large flowers positioned above and beyond the foliage.

*Growth and branching habit.*—Freely branching habit; dense and full plant habit; typically about ten lateral branches develop per plant; pinching, that is, removal of the terminal apices, is usually not required. Vigorous growth habit.

*Plant height.*—About 18 to 21 cm.

*Plant width (spread).*—About 30 to 35 cm.

*Lateral branch description.*—Length: About 15 to 18 cm. Diameter: About 6 to 8 mm. Internode length: About 3 to 4 cm. Color: 146B; towards the leaf nodes, 185D.

*Foliage description.*—Arrangement: Alternate or whorled; simple. Length: About 11 to 12 cm. Width: About 4 cm. Shape: Lanceolate to narrowly ovate. Apex: Acuminate. Base: Acute. Margin: Entire with ciliation. Texture, upper and lower surfaces: Glabrous, smooth. Venation pattern: Pinnate. Color: Developing foliage, upper surface: 146A. Developing foliage, lower surface: 146B. Fully expanded foliage, upper surface: 147A. Fully expanded foliage, lower surface: 147B. Venation, upper surface: 147C. Venation, lower surface: 146B. Petiole length: About 1.5 cm. Petiole diameter: About 3 mm. Petiole color: 146B, tinged with 185D.

Flower description:

*Flower type and flowering habit.*—Single, large, rounded, flat and redpurple-colored flowers. Freely flowering habit, usually about one flower per leaf axil. Flowers positioned above and beyond the foliage and typically face upward or outward. Flowers last about two weeks on the plant depending on environmental conditions. Petals self-cleaning; gynoecium persistent. Flowers not fragrant.

*Flowering season.*—Year-round under greenhouse conditions. In the garden, flowering from spring until fall. Flowering indeterminate and continuous.

*Flower diameter.*—About 7.5 cm.

*Flower buds.*—Rate of opening: From flower bud to fully open flower, typically about five to seven days depending on temperature. Length: About 2 cm. Diameter: About 1.5 cm. Shape: Ellipsoidal. Color (just before opening): 58B.

*Petals.*—Quantity: Single, five per flower, imbricate. Length: Banner and lateral petals: About 3 cm. Basal petals: About 4 cm. Width: About 3.5 to 4 cm. Shape: Roughly cordate. Apex: Emarginate. Base: Rounded. Margin: Entire. Texture, upper and lower surfaces: Smooth; satiny. Color: When opening, upper surface: 57A. When opening, lower surface: 58B. Fully opened, upper surface: 57B; color does not fade with development. Fully opened, lower surface: 58B.

*Spur.*—Length: About 4.5 cm. Color: 185B.

*Peduncles.*—Length: About 5 cm. Strength: Strong, flexible. Angle: About 45° from vertical. Color: 146C; tinged with 185C.

*Reproductive organs.*—Androecium: Stamen number: Five fused at anthers, filaments free, hooded. Anther length: About 5 mm. Anther shape: Obovate. Anther color: 57A. Amount of pollen: Abundant. Pollen color: 155A. Gynoecium: Pistil number: One, five-segmented. Pistil length: About 5 mm. Stigma color: Close to 158A. Style color: Yellowish green. Ovary color: 146A, tinged with 185C.

*Fruit/seed development.*—Fruit and seed development has not been observed.

Disease/pest resistance: Plants of the new Impatiens have not been observed to be resistant to pathogens and pests common to Impatiens.

Light & temperature tolerance: In outdoor nursery trials in Connellsville, Pa., plants of the new Impatiens have been observed to be tolerant to full sun conditions and high temperatures (32 to 38° C.) during the summer. In outdoor nursery trials in Lompoc, Calif., plants of the new Impatiens have been observed to be tolerant to low night temperatures from about 5 to 10° C.

It is claimed:

1. A new and distinct cultivar of New Guinea Impatiens plant named 'Ovation Cherry Rose', as illustrated and described.

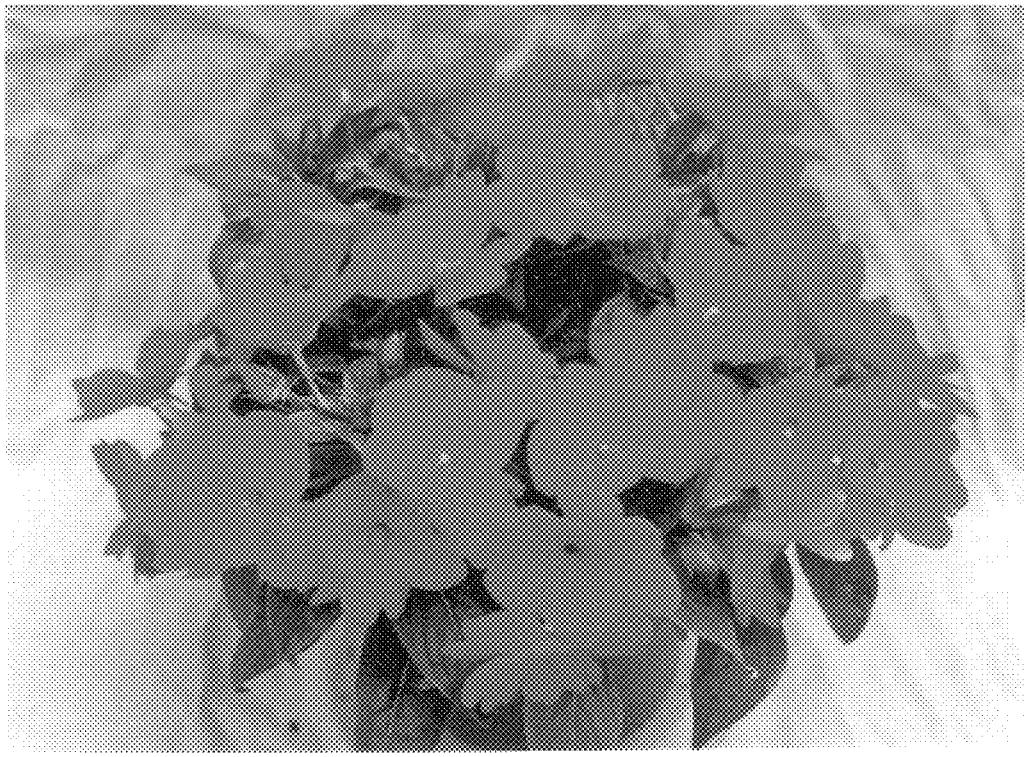

* * * * *